(12) United States Patent
Ross et al.

(10) Patent No.: US 10,966,858 B2
(45) Date of Patent: Apr. 6, 2021

(54) SUPPORT STRUCTURE

(71) Applicant: University of Strathclyde, Glasgow (GB)

(72) Inventors: Karyn Ross, Glasgow (GB); Emma Henderson, Glasgow (GB); Mark O'Hare, Glasgow (GB); Nicola J. Cairns, Glasgow (GB); Alejandra Aranceta Garza, Glasgow (GB)

(73) Assignee: University of Strathclyde, Glasgow (GB)

( * ) Notice: Subject to any disclaimer, the term of this patent is extended or adjusted under 35 U.S.C. 154(b) by 575 days.

(21) Appl. No.: 15/504,422

(22) PCT Filed: Aug. 19, 2015

(86) PCT No.: PCT/GB2015/052414
§ 371 (c)(1),
(2) Date: Feb. 16, 2017

(87) PCT Pub. No.: WO2016/027090
PCT Pub. Date: Feb. 25, 2016

(65) Prior Publication Data
US 2017/0231800 A1 Aug. 17, 2017

(30) Foreign Application Priority Data
Aug. 19, 2014 (GB) .................................... 1414720

(51) Int. Cl.
*A61F 5/058* (2006.01)
*A61F 5/01* (2006.01)
*A61F 7/00* (2006.01)

(52) U.S. Cl.
CPC ........ *A61F 5/05866* (2013.01); *A61F 5/0118* (2013.01); *A61F 7/00* (2013.01)

(58) Field of Classification Search
CPC ...... A61F 5/05866; A61F 5/0118; A61F 7/00; A61F 5/01; A61F 5/05; A61F 5/013;
(Continued)

(56) References Cited

U.S. PATENT DOCUMENTS

| 1,469,315 A | * | 10/1923 | Hansard | ................ A61F 5/0118 473/213 |
| 3,788,307 A | * | 1/1974 | Kistner | ............... A61F 5/05866 602/21 |

(Continued)

FOREIGN PATENT DOCUMENTS

| DE | 3519493 A1 | 12/1986 |
| DE | 202006013694 U1 | 12/2006 |

(Continued)

OTHER PUBLICATIONS

Office Action for European Application No. 15762665.6 dated Feb. 7, 2019, 5 pages.

(Continued)

*Primary Examiner* — Ophelia A Hawthorne
*Assistant Examiner* — Caitlin A Carreiro
(74) *Attorney, Agent, or Firm* — Alston & Bird LLP

(57) ABSTRACT

A support and corresponding system and method of using and producing the support, the support being for supporting a joint or body part of a wearer, the support having at least one rigid first support member, at least one fixing device for attaching the support to the wearer, and at least one second support member extending at an angle from the first support member. Optionally, the joint is a joint between first and second body parts, and the first body part is movable or pivotable relative to the second body part via the joint, and the support is arranged such that at least one of the fixing devices is operable to fix the support to the first body part, the at least one rigid support member covers at least part of (Continued)

at least one side of the first body part and extends over at least part of at least one side of the joint, the second support member is configured to extend to another side of the second body part to the first support member, the first support member is adapted to limit motion of the second body part and/or joint in a first direction, and the second support member is configured to limit motion of the second body part in a second direction.

26 Claims, 11 Drawing Sheets

(58) Field of Classification Search
CPC ............. A61F 5/05858; A61F 13/107; A41D 19/01582; A41D 19/01588; A41D 13/081
USPC .......... 602/21, 64, 14, 5, 20, 1, 2, 6, 16, 22; 128/878, 879, 877; 2/16, 162; D24/190
See application file for complete search history.

(56) References Cited

U.S. PATENT DOCUMENTS

| | | | |
|---|---|---|---|
| 4,732,142 A * | 3/1988 | Hurlburt | A61F 5/0118 602/21 |
| 4,768,502 A * | 9/1988 | Lee | A61F 5/05866 602/20 |
| 4,862,877 A | 9/1989 | Barber | |
| 5,121,743 A | 6/1992 | Bishop | |
| 5,417,645 A | 5/1995 | Lemmen | |
| 5,725,489 A * | 3/1998 | Bar-Or | A61F 5/05866 602/16 |
| 5,971,945 A * | 10/1999 | Garris | A61F 5/05866 602/21 |
| 6,007,505 A * | 12/1999 | Grim | D04B 1/22 602/6 |
| 6,186,966 B1 * | 2/2001 | Grim | D04B 1/22 602/6 |
| 6,913,582 B2 * | 7/2005 | Chen | A61F 5/05866 128/878 |
| 2005/0165338 A1* | 7/2005 | Iglesias | A61F 5/0118 602/21 |
| 2006/0015980 A1* | 1/2006 | Nordt, III | A41D 13/088 2/16 |
| 2014/0024987 A1* | 1/2014 | Anglada | A61F 5/013 602/16 |
| 2014/0330183 A1* | 11/2014 | Kazemtabrizi | A61F 5/0118 602/12 |
| 2015/0374529 A1* | 12/2015 | Summit | A61F 5/0118 602/22 |

FOREIGN PATENT DOCUMENTS

| | | |
|---|---|---|
| EP | 1452154 A2 | 9/2004 |
| WO | WO 2014/070625 A1 | 5/2014 |

OTHER PUBLICATIONS

International Searching Authority, International Search Report and Written Opinion for International Application No. PCT/GB2015/052414, dated Feb. 2, 2016, 18 pages, European Patent Office, Netherlands.
Intellectual Property Office, Search Report for Application No. GB1414720.1, Feb. 16, 2015, 4 pages, Great Britain.

* cited by examiner

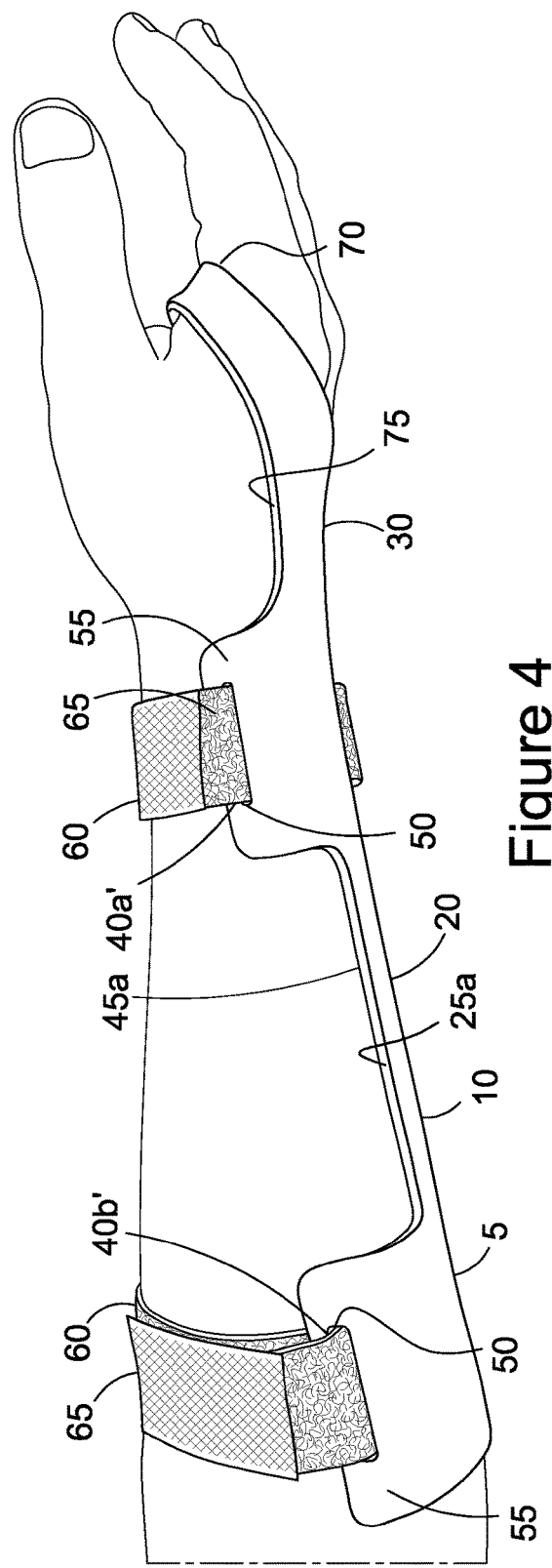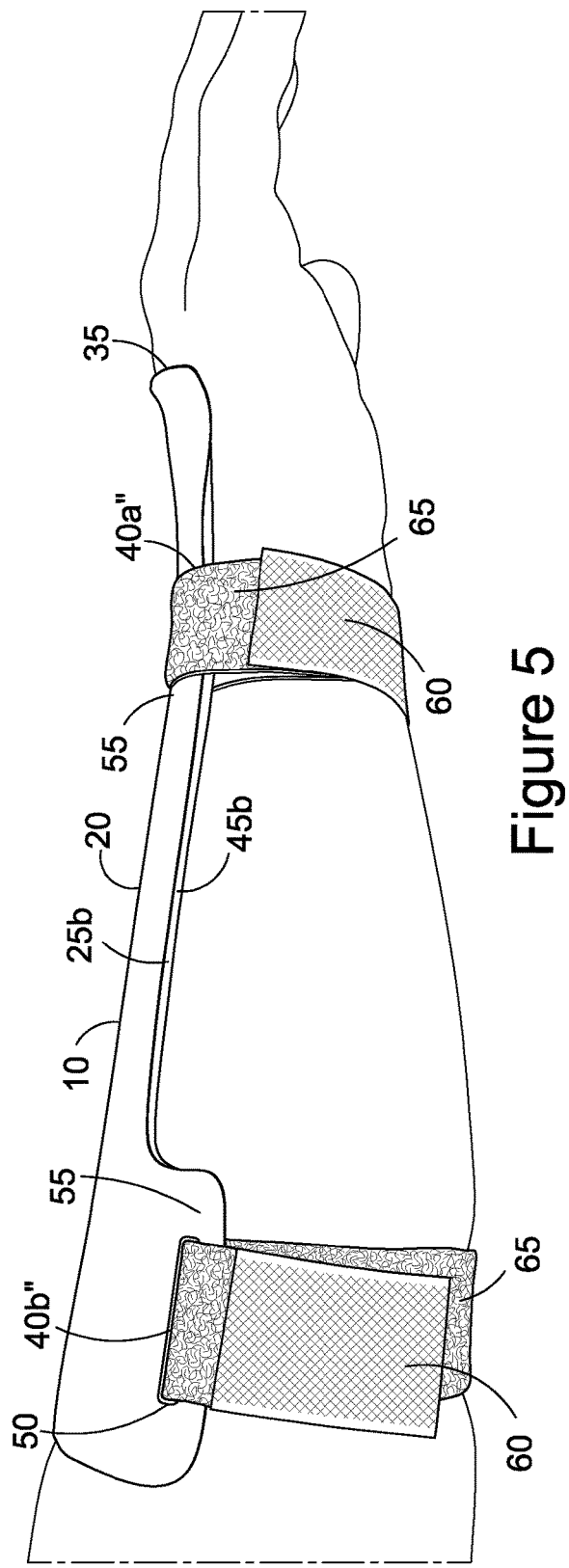

SUPPORT STRUCTURE

CROSS REFERENCE TO RELATED APPLICATIONS

This application is a National Stage Application, filed under 35 U.S.C. 371, of International Application No. PCT/GB2015/052414, filed Aug. 19, 2015, which claims priority to Great Britain (GB) Application No. 1414720.1, filed Aug. 19, 2014; the contents of both of which are hereby incorporated by reference in their entirety.

BACKGROUND

Related Field

The present invention relates to a support structure for supporting a joint or body part, particularly to a wrist support structure such as a wrist-hand splint.

Description of Related Art

A wrist-hand splint is a support structure that is worn around part of the hand and forearm in order to maintain the wrist in a clinically appropriate position, for example, in order to relieve pain in Rheumatoid Arthritis sufferers. The splint restricts motion of the joint.

However, such splints can suffer from a variety of problems. For example, it can be difficult to adjust the splint to securely fit to the forearm of the patient, at least without custom manufacture. Furthermore, the required wrist position is often not maintained during rest and/or during activity. In some designs of splint, the grip strength can be significantly reduced. In addition, with some splint designs, the splint can interfere with the hand and/or objects being held, gripped or manipulated using the hand. Some designs of splint can be heavy and unwieldy. Some designs of splint can be difficult to clean.

BRIEF SUMMARY

According to an aspect of the invention is a support for supporting a joint or body part of a wearer, the support having at least one rigid first support member, at least one fixing device for attaching the support to the wearer, e.g. to a body part of the wearer, and at least one second support member extending at an angle from the first support member.

The at least one second support member may be or comprise a rigid second support member.

The joint may be a joint between a first and second body parts. The first body part may be movable and/or pivotable relative to the second body part via the joint. The support may be arranged such that at least one of the fixing devices is operable to fix the support to the first body part. The at least one first support member may cover at least part of at least one side of the first body part and may extend over at least part or all of at least one side of the joint and may cover a part of at least one side of the second body part. The second support member may be configured to extend to another side of the second body part, e.g. an opposite side of the second body part to the first support member. The first support member may be adapted to limit motion of the second body part and/or joint in a first direction and the second support member may be configured to limit motion of the second body part in a second direction, which may be opposite to the first direction. The second support member may be configured to limit motion of the second body part in at least two directions, which may be generally perpendicular to each other.

The support may be or comprise a medical support such as a wrist support or wrist-hand splint. The first body part may be or comprise a forearm. The second body part may be or comprise a hand. The joint may be or comprise a wrist.

The support may be configured to limit flexion and/or extension of the wrist. The first support member may be configured to limit extension of the wrist. The second support member may be configured to limit flexion of the wrist. The support may be configured to limit radial deviation of the wrist, e.g. deviation in at least one lateral and/or transverse direction.

The second support member may be integral with the first support member.

All or part of the first support member may be configured to be located above and/or on an upper or top surface of the body part, e.g. the first body part, or the joint, e.g. in use.

The second support member may be configured to extend obliquely from the first support member, e.g. from a bending, curved or sloping section of the first support member. The second support member may be configured to extend forwardly, downwardly and/or laterally from the first support member, e.g. from the bending, curved or sloping section of the first support member. In use, the second support member may be arranged to extend between a thumb and index finger of the wearer. The second support member may be arranged to extend along at least part of the palm in use, e.g. to a central portion of the palm or palmer arch, for example to the deep palmer arch or superficial palmer arch.

The first support member may comprise the bending, sloping or curved section, which may bend, curve or slope in a longitudinal direction of the first support member. The bending, sloping or curved section may be provided at an end of the first support member, e.g. a forward or front end. The support may be configured such that, in use, the bending, sloping or curved section is provided at, over or covering at least a part of the at least one side (e.g. an upper or top side) of the joint and/or a part of the at least one side (e.g. an upper or top side) of the second body part. The bending, sloping or curved section may be configured to produce an angle between the first and second body parts of between 5 and 30°, e.g. between 10 and 20°. The bending, sloping or curved section may be angled between 5 and 30°, e.g. between 10 and 20° from another part, e.g. an adjacent part, of the first support member.

The second support member may be provided at or toward an end of the first support member, such as a forward or front end. The second support member may extend from the bending, sloping or curved section of the first member, e.g. from a lateral or side portion of the sloping or curved section of the first member.

At least part, such as a first part, of the second support member may extend obliquely from the first support member. At least part, such as the first part, of the second support member may extend obliquely forwardly, downwardly and/or laterally outwardly and/or away from the first support member. At least part, such as a second part, of the second support member may extend laterally, e.g. generally parallel to at least part of the first support member, such as a centre or flatter part. The first part of the second support member may extend from the first support member. The second part of the second support member may extend from the first part of the second support member. At least part, such as the first and/or second parts, or all of the second support member may extend and/or be located forwardly of the first support member. The second part of the second support member may be spaced apart from the first support member in at least one, two or more perpendicular directions, e.g. forwardly and downwardly.

At least part, e.g. the first and/or second part, or all of the second support part may be curved. The second support member may define a generally "L" shape. The second support member and optionally part of the first support member may define at least part or all of a C-shaped profile in at least one direction, e.g. in a plane extending obliquely, forwardly and/or perpendicularly from the first support member. The second support part may define a hook or other retainer, which may be configured to retain the hand.

A distal end of the second support member, e.g. distal relative to the first support member, may comprise a rounded, domed and/or hemispherical portion, and may project toward the palm in use, and/or upwardly and/or toward the first support member. The rounded, domed and/or hemispherical portion may be a hollow, bowled or spooned portion. The second support portion may terminate at the distal end. The distal end of the second support portion may be a free or open end, e.g. it may not be connected or directly connected to the first support portion, e.g. other than by the first part of the second support member.

A portion of the second support member, e.g. the first part of the second support member, that is located towards, adjacent or is connected to the first support member may reduce in width, e.g. towards an intermediate or middle portion of the second support member, which may be a part of the second support member that is located or locatable between the thumb and index finger in use. The width of the second support member may increase from the intermediate portion towards or at the distal end and/or the rounded, domed and/or hemispherical portion of the second support member.

The second support member may be configured to conform to or follow a shape and/or contours of at least part of the hand and/or palm. In use, the first and second support members may be configured such that at least part of the hand lies between part of the second support member (e.g. the second part and/or distal end of the second support member) and the first support member (e.g. the bending, sloping or curved section of the first member).

The support may comprise one or more fixings devices, which may be comprised in one, two or more pairs of fixing devices. One or more or each pair of fixing devices may comprise opposing fixing devices, e.g. extending from opposing sides (such as opposite lateral sides) of the first support member.

Opposing fixing devices of at least one of the pairs of fixing devices, such as a forwardmost pair of fixing devices and/or at least one or each pair of fixing devices located closest or towards the second support member, may extend to different lateral extents from the first support member. The fixing device of at least one or each pair of fixing devices, such as a forwardmost pair of fixing devices and/or at least one or each pair of fixing devices located closest or towards the second support member, that extends to the opposite side of the first support member to the side of the first support member from which the second support member extends may extend laterally less than the other of the pair of fixing devices. The support may be configured such that, in use, at least one or each of the fixing devices on the ulnar side of the wrist does not extend as far as the opposing fixing device. The support may be configured such that, in use, the ulnar side of the wrist and the ulnar side of the hand are not inhibited by the support. The support may be configured such that, in use, the rigid portion of the support does not extend to the ulnar side of the wrist and/or the ulnar side of the hand.

The support may be arranged such that at least a part of the support, e.g. a forward side part and/or a part of the support that is toward or comprises the second support member, which may be or comprise the one or more fixing devices and/or at least a part of the first and/or second support member, does not cover a side, e.g. lateral side, or ulnar side of the forearm, wrist and/or hand, in use.

At least a part of the support, e.g. a forward side part and/or a part of the support that is toward or comprises the second support member, which may be or comprise the one or more fixing devices and/or at least a part of the first and/or second support member, may comprise only fixing devices extending from a lateral side of the first support member in which the second support member extends. At least a part of the support, e.g. a forward side part and/or a part of the support that is toward or comprises the second support member, which may be or comprise the one or more fixing devices and/or at least a part of the first and/or second support member, may comprise no fixing devices or other rigid structure extending from a lateral side of the first support member opposite to that from which the second support member extends, i.e. an ulnar side of the hand, wrist and/or forearm, in use. The at least one fixing device may comprise at least one flange, slot, and/or other attachment for mounting a strap or other fixing. The at least one flange, slot, and/or other attachment for mounting a strap or other fixing may be rigid. At least one or each of the fixing devices may comprise a protruding flange that extends from the first support member, e.g. from a side/lateral edge of the first support member. At least one of the slots and/or other attachments may be provided in respective protruding flanges. The protruding flanges may be arranged to, in use, extend around at least part of the forearm from the first support member. The at least one fixing device may be configured to receive or be connected to or comprise a strap. The strap may comprise at least one fixing mechanism for releasably fixing the strap to itself, another strap and/or flanges of one, two or more fixing devices. The fixing mechanism(s) may comprise Velcro, e.g. low-tack Velcro, popper fixing, a buckle, a clasp and/or the like. The strap(s) or at least one fixing device may be configured to extend around the arm or forearm. The strap(s) may be removable from at least one or each of the flange(s).

The at least one fixing device may comprise a fixing member, such as a resiliently deformable or bendable member, which may be curved, and may be adapted to extend downwardly and/or, in use, extend at least part of the way around a wrist and/or fore-arm, e.g. to an underside of the forearm and/or wrist of the wearer. The support may comprise at least two spaced apart fixing devices or pairs of fixing devices, which may be spaced apart longitudinally along the first support member.

The support may be configured such that the thumb of the wearer may be located or locatable, in use, between one of the fixing devices and the second support member.

The support may be configured such that, other than the two or more discrete or spaced apart fixing devices, it does not encircle or enclose the forearm or wrist of the wearer in use.

The first support member may be or comprise an elongate member. The first support member may comprise a metallic member, such as a metal bar or strip. The first and/or second support member may comprise a polymeric or silicone member, coating or portion. The first and/or second member may comprise a composite member or portion, e.g. a fiber reinforced polymer or resin matrix, such as a carbon fiber or glass fiber matrix. The first and/or second support members may be formed from or comprise a non-elastic material.

At least part or all of the first and/or second support member may comprise one or more portions or layers formed from a different material than one or more other portions or layers of the first and/or second support member.

At least part of the first and/or second support member, e.g. at least one portion or layer, may comprise a softer and/or more pliable and/or deformable material. At least part of the first and/or second support member, e.g. at least one portion or layer, may comprise a rigid and/or less pliable or deformable material. The rigid and/or less pliable or deformable material may be or be comprised in an inner material, portion or layer. The softer and/or more pliable and/or deformable material may be or may be comprised in an outer material, portion, coating or layer. For example, the inner material, portion or layer and/or rigid/less pliable material, portion or layer may comprise a metallic material, a rigid polymeric material and/or a composite material, such as fiber reinforced composite and/or the like. The outer and/or softer/more pliable material, portion, coating or layer may comprise a bendable, compressible or pliable polymeric material, a silicone based material and/or a fabric material and/or the like. The outer and/or softer/more pliable material, portion, coating or layer may be provided at least, or only, on a portion of the second support member and/or the distal end and/or the rounded, domed and/or hemispherical portion of the second support member, e.g. a portion that is on a side opposite to the first support member or hand, in use. The outer and/or softer/more pliable material, portion, coating or layer may conform to external objects to improve contact with external objects. At least part of the support may be provided with or covered by at least one sleeve, such as a fabric sleeve, which may be removable and/or detachable from the support. The sleeve may be separately washable from the support. The fabric sleeve may comprise a padded and/or compressible material. The sleeve may be or comprise an under sleeve, which may be located or locatable between at least part of the first and/or second support members and the wearer. The sleeve may be or comprise an over-sleeve, which may be configured to cover at least part or all of an outer surface of the support.

At least part of the support and/or the sleeve may be printed or dyed and/or otherwise coloured and/or marked.

At least part or all of the support, sleeve or cover may comprise, for example, one or more layers of fabric, padding such as gel, fibre or fabric padding or wadding, and/or the like.

The support and/or sleeve may be provided with one or more pockets, chambers and/or the like. The pockets or chambers may be provided with or adapted to receive heat and/or cool pads and/or the like.

At least part or all of the second support member and/or the first support member may be formed from a flattened or sheet like member.

According to a second aspect of the present invention is a fabric sleeve or cover configured to be mounted to or used with a support, e.g. a medical support such as a wrist support or wrist-hand splint. The support may be or comprise a support according to the first aspect. The sleeve or cover may be or comprise a fabric sleeve or cover. The sleeve or cover may be releasably attachable to the support. The sleeve or cover may be configured to cover or contact at least part of the hand and/or support.

The sleeve or cover may be or comprise an under sleeve or cover, which may be located or locatable between at least part of the first and/or second support members and the wearer. The sleeve or cover may be or comprise an over-sleeve or cover, which may be configured to cover at least part or all of an outer surface of the support.

At least part of the sleeve or cover may be printed or dyed and/or otherwise coloured and/or marked.

The sleeve or cover may comprise, for example, one or more layers of fabric, padding such as gel, fibre or fabric padding or wadding, and/or the like.

The sleeve may be provided with one or more pockets, chambers and/or the like. The pockets or chambers may be provided with or adapted to receive and/or retain heat or cool pads and/or the like.

According to a third aspect of the present invention is a system comprising a support according to the first aspect and a sleeve or cover according to the second aspect. The sleeve or cover being adapted to cover at least part or all of the support and/or is located or locatable between at least part of the first and/or second support members of the support and the wearer of the support. The sleeve or cover may be selectively attachable to and/or removable from the support.

According to a fourth aspect of the present invention is a method for holding a wrist and/or hand in a given position, the method comprising fitting a support according to the first aspect and/or a system according to the third aspect, the method comprising fitting at least part of the support to a forearm and/or wrist such that the first supporting member is provided on an upper surface of the forearm and/or wrist and locating the second support member such that it extends between a thumb and an index finger to a location against, proximate or below the palm of the hand.

According to a fifth aspect of the present invention is a method of manufacturing a support according to a first aspect and/or a system according to the second aspect. The method may comprise moulding, laying material up on a former or template, 3D printing, injecting, bending, bonding, fixing and/or cutting material so as to form at least one elongated, rigid first support member and at least one second support member extending at an angle from the first support member, e.g. such that the second support member extends and/or curves forwardly and downwardly from the first support member and then laterally relative to the first support member.

According to a sixth aspect of the present invention is an arm/support assembly, comprising a support of the first aspect and/or a system of the third aspect mounted on a forearm, wrist and/or hand of a wearer.

It should be understood that the individual features and/or combinations of features defined above in accordance with any aspect of the present invention or below in relation to any specific embodiment of the invention may be utilised, either alone or in combination with any other defined feature, in any other aspect or embodiment of the invention. Furthermore, the present invention is intended to cover apparatus configured to perform any feature described herein in relation to a method and/or a method of using or producing or manufacturing any apparatus feature described herein.

BRIEF DESCRIPTION OF THE FIGURES

These and other aspects of the present invention will now be described, by way of example only, with reference to the accompanying drawings, in which:

FIG. 4 is an elevation or side view of the wrist support of FIG. 1, in use;

FIG. 5 is an elevation or side view of the opposite side of the wrist support of FIG. 1, in use;

DETAILED DESCRIPTION OF VARIOUS EMBODIMENTS

Figure 7:
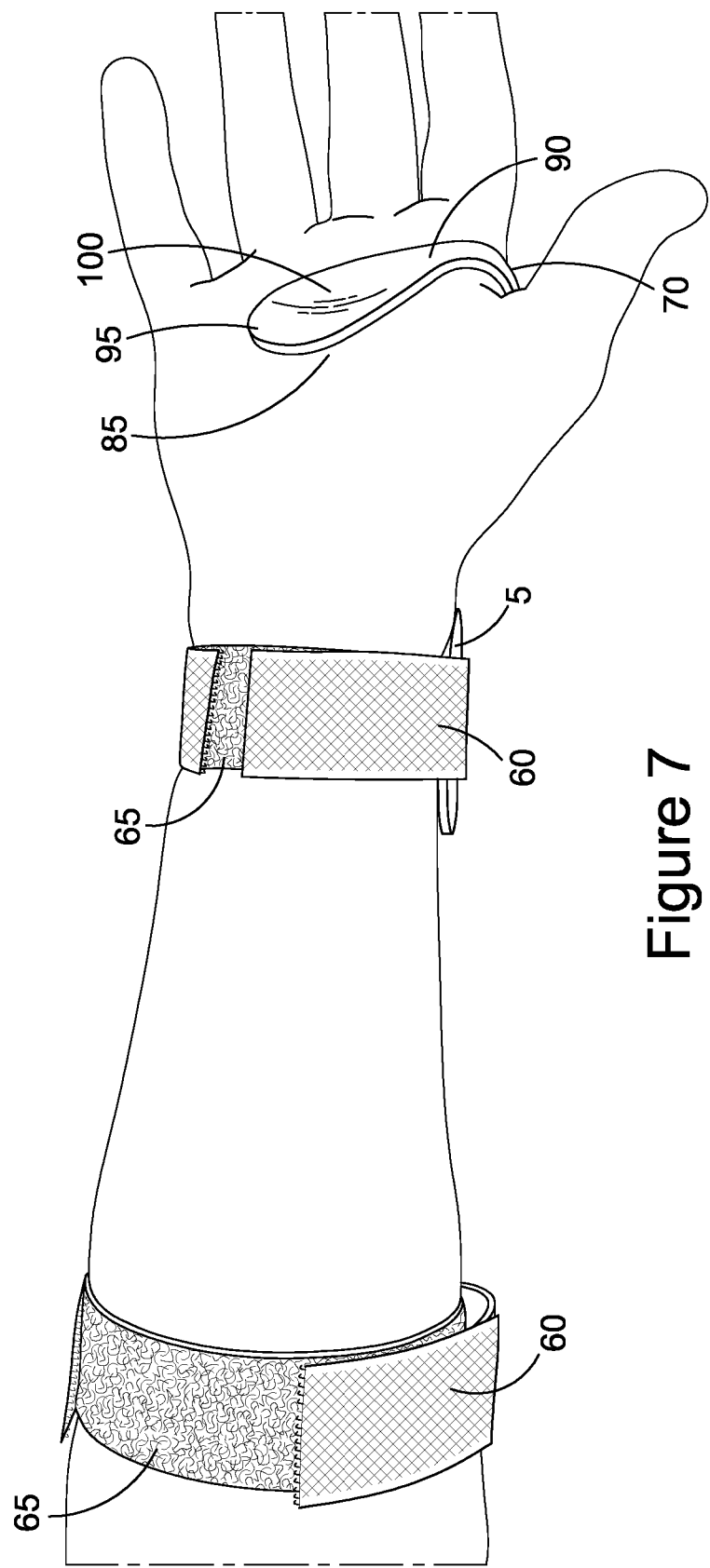
FIG. 7 is a bottom view of the wrist support of FIG. 1, in use.
Figure 8:
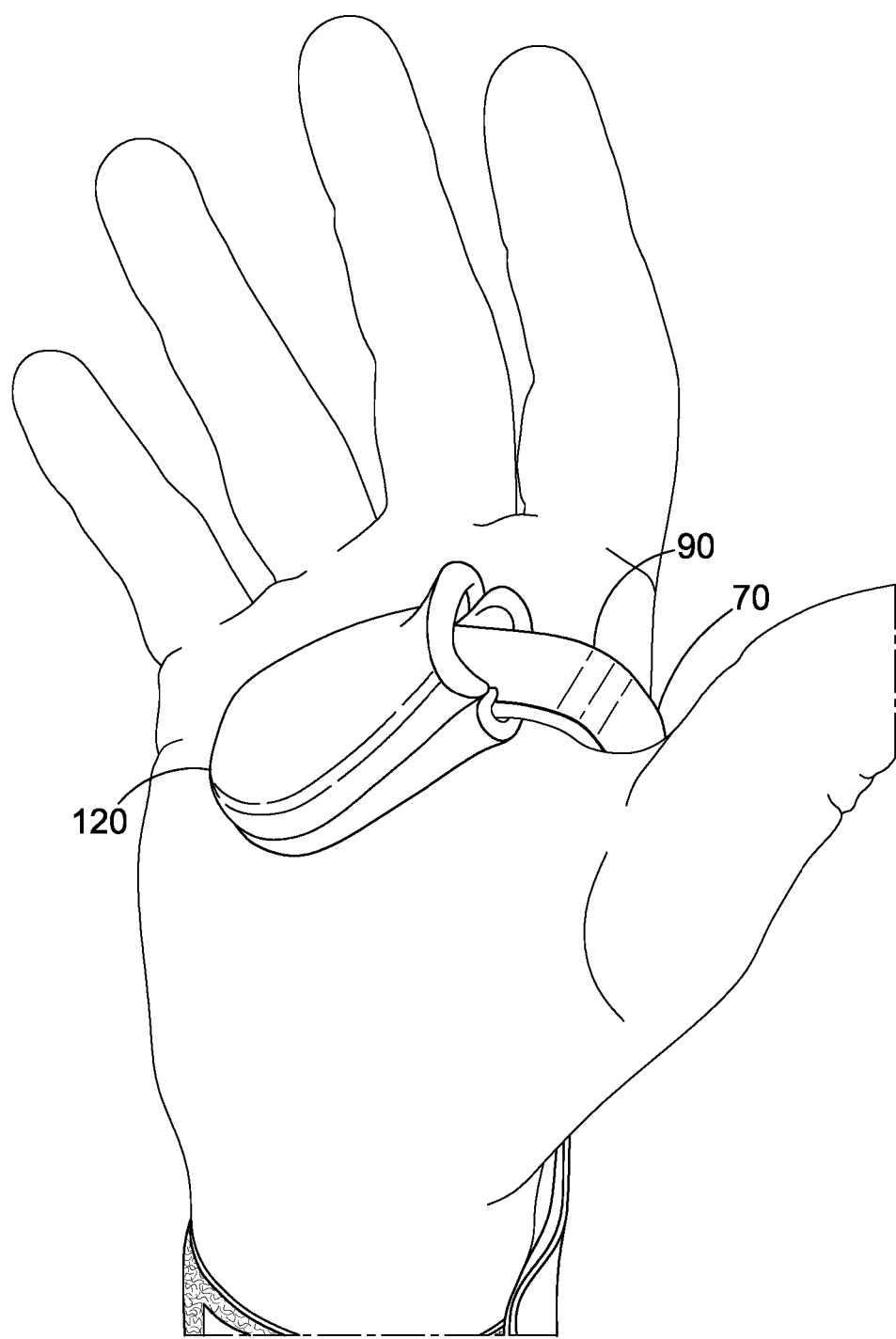
FIG. 8 is a detailed bottom view of a second support member of the wrist support of FIG. 1 with a cover, in use.

FIGS. 1 to 8 and 10 to 13 show a support device 5 in the form of a wrist support or wrist-hand splint which is worn around part of the forearm and wrist so as to support the wrist in a clinically appropriate position (see particularly FIGS. 4, 5 and 7). Such wrist supports or wrist-hand splints can be used to alleviate pain caused by Rheumatoid Arthritis, for example.

Figure 1:
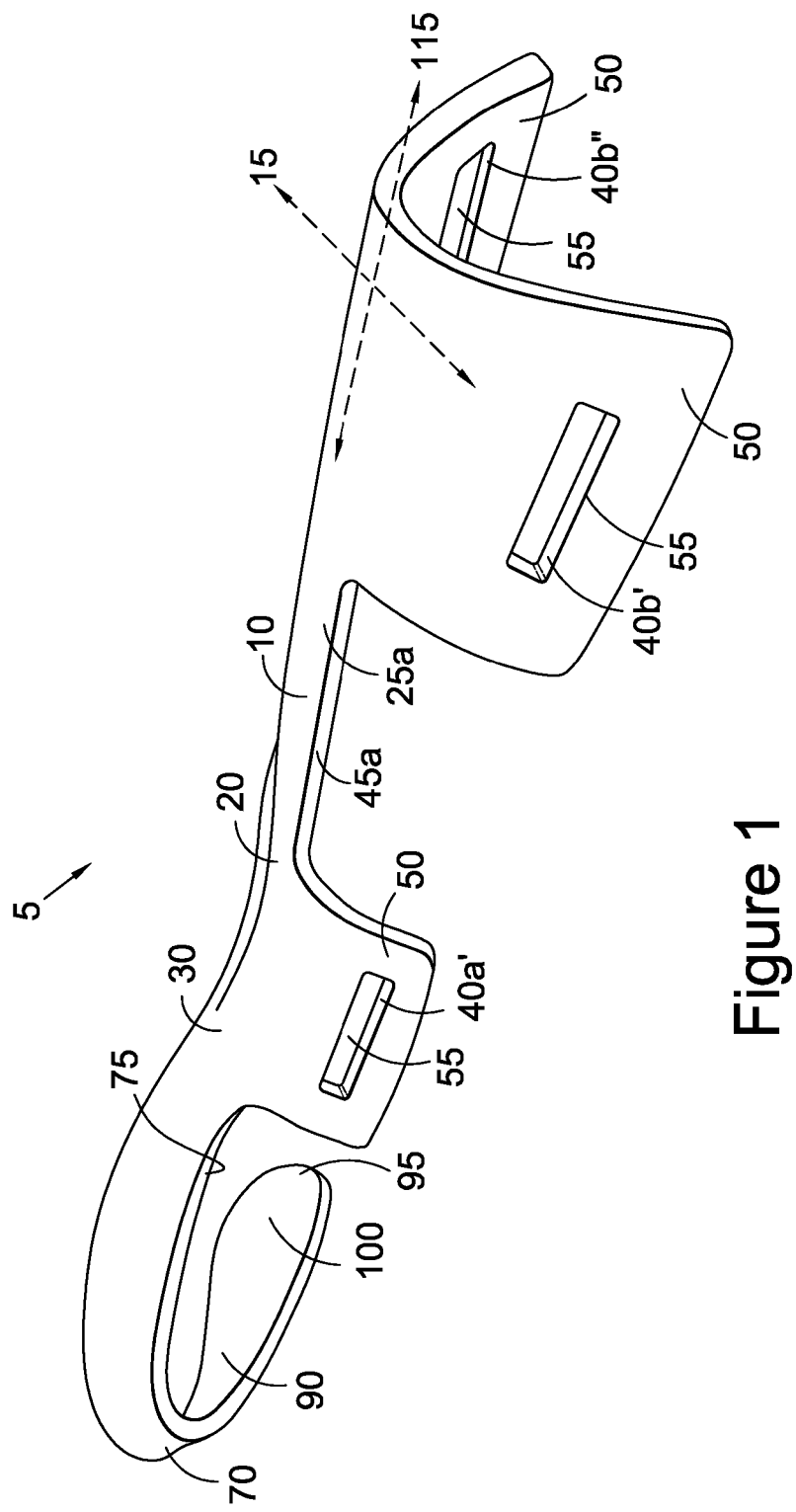
FIG. 1 is perspective view of a wrist support.
Figure 2:
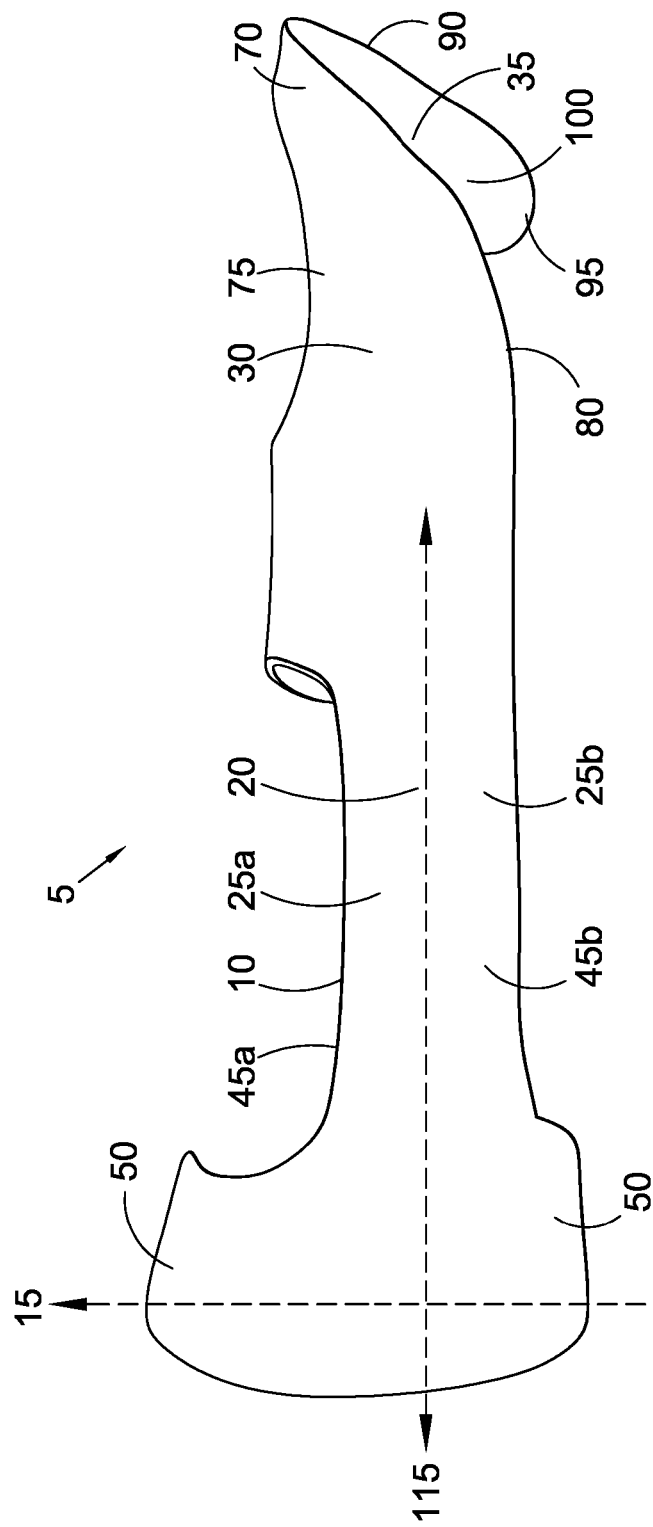
FIG. 2 is a plan or top view of the wrist support of FIG. 1.
Figure 3:
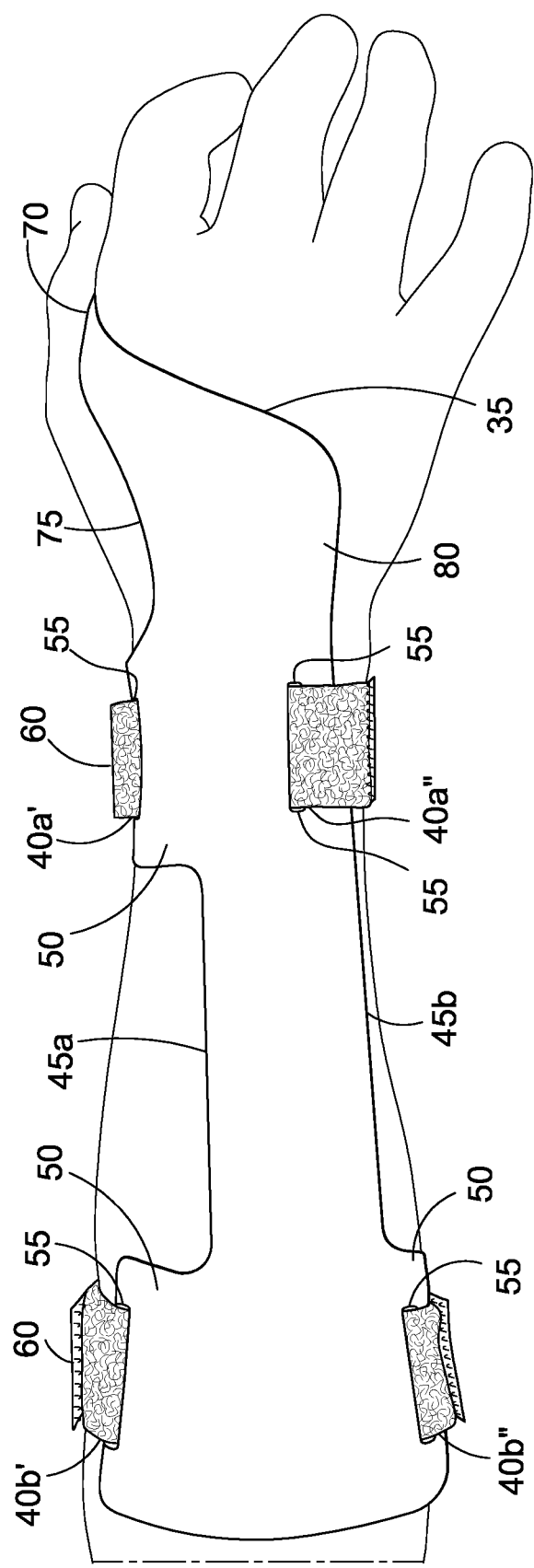
FIG. 3 is a plan or top view of the wrist support of FIG. 1, in use.
Figure 6:
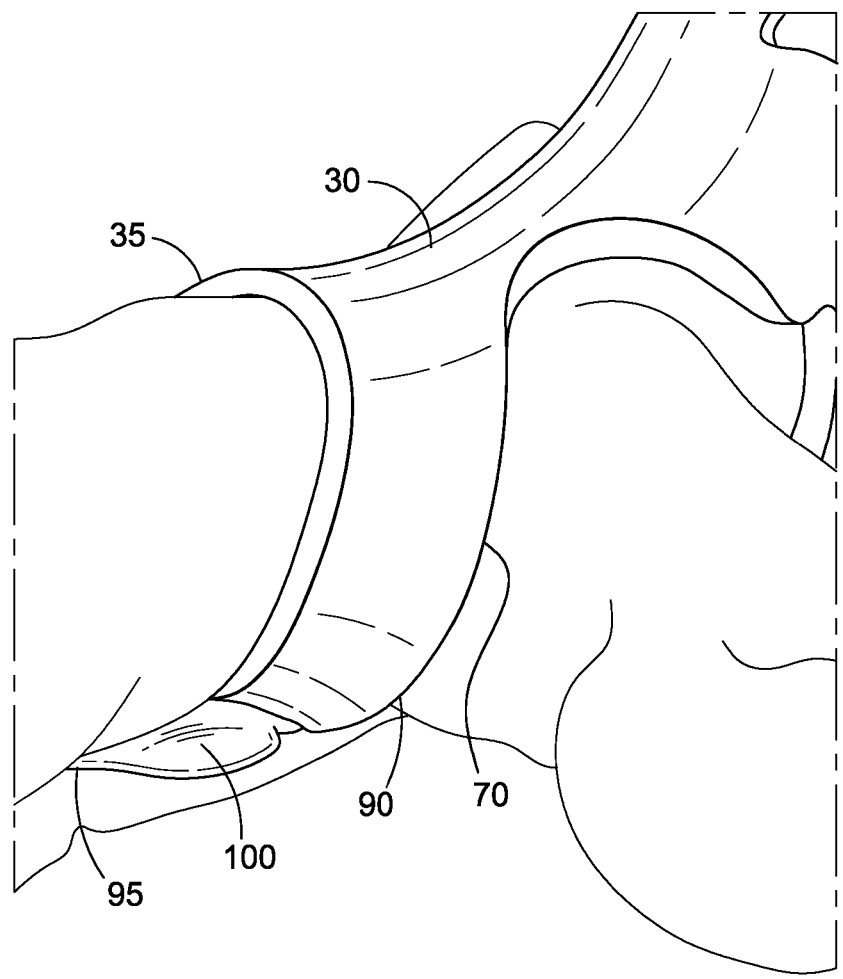
FIG. 6 is a detailed view of a second support member of the wrist support of FIG. 1, in use.

The support device 5 comprises an elongated rigid first support member 10 that is configured to extend along an upper surface of a wearer's forearm and wrist (see FIG. 3).

The first support member 10 can be formed from a rigid polymer, a composite material, an elongate metallic member and/or other suitable material. However, the first support member 10 as a whole is preferably non-elastic.

For example, in one embodiment, the first support member 10 is moulded into a suitable shape using a Nylon/glass fibre composite matrix. In another embodiment, the first support member 10 is formed in a multi-layer construction comprising a core or one or more inner layers formed from a more rigid material, such as a metallic, polymeric or composite material and one or more outer layers or coatings of softer materials, such as a polymeric material, silicone, and/or the like. In this way, it may be possible to provide the required support and rigidity whilst at the same time making the support device 5 comfortable to wear.

The first support member 10 has a cross section in a transverse or lateral direction 15 (see FIGS. 1 and 2) that is configured to proximate the upper shape of the forearm. As such, the first support member 10 comprises a longitudinally extending centre part 20 towards the centre of the first support member 10 in the transverse or lateral direction 15. The support device 5 is configured such that, in use, the centre part 20 sits on top of the forearm and wrist of the wearer (see FIGS. 3 to 5). The first support member further comprises a pair of curved parts 25a, 25b, which respectively extend from each lateral side of the centre part 20. The curved parts 25a, 25b are arranged to extend downwardly around a curved part of the upper or top surface of the forearm and optionally part of the way round the sides of the forearm in use. It will be appreciated that the centre part 20 may be flatter or less curved or radiused than the curved parts 25a, 25b. It will also be appreciated that the cross sectional profile of the first support member in a lateral direction 15, e.g. the dimensions and/or curvature of the centre part 20 and/or the curved parts 25a, 25b, can vary along the length of the first support member 10.

The first support member 10 transitions into a ramped or sloping part 30 at one end 35, e.g. a front or forward end, thereof. The sloping part 30 is arranged to cover the upper side of the wrist, and optionally also a portion of the upper hand, in use (see FIGS. 3 to 6). The ramped or sloping part 30 is configured to hold the hand and wrist at an angle of between 5 and 30°, e.g. between 10 and 20° relative to the upper surface of the forearm. For example, the ramped or sloping part 30 may extend at a corresponding angle relative to another and/or adjacent part of the first support member 10, e.g. the centre part 20, although it will be appreciated that the ramped or sloping part 30 need not necessarily be at the same angle as the wrist in order to hold the wrist at the required angle.

The support device 5 further comprises a second support member 70 at one end, i.e. the front or forward end 35 of the first support member. The second support member 70 is integral with the first support member 10 and extends from one side or edge 75 of the ramped or sloping part 30 of the first support member 10. In use, the second support member 70 is arranged to extend from the first support member 10 forwardly and downwardly between the thumb and index finger of the wearer's hand and then round to a position adjacent the palmer arch 85 of the palm, where it terminates (see FIGS. 6 and 7).

In particular, the second support member 70 extends obliquely forwardly and laterally outwards from the first support member 10 and also curves downwardly from the first support member 10 to a position spaced apart from, e.g. lower than, the ramped or sloping section 30 of the first support member 10. Thereafter, the second support member 70 extends generally laterally in a direction parallel to the lateral or transverse direction 15 of the first support member so as to project part of the way back towards a position corresponding with a side 80 of the first support member 10 that is opposite to the side 75 of the first support member 10 from which the second support member 70 extends. In this way, the ramped or sloping part 30 and the second support member form a cross section similar to a 'C' shape in a laterally and obliquely forwardly extending plane and/or when seen from the front (see e.g. FIG. 6).

The second support member 70 reduces in thickness as it extends from the first support member 10 towards an intermediate portion 90 of the second support member 70 before increasing in thickness again at a distal or terminal end 95 of the second support member 70. In this way, the second support member 70 is relatively wide where it junctions with the first support member 10 to provide strength at the junction, before reducing in width at an intermediate portion 90 for passing between the wearer's thumb and index finger in use, so as to minimise interference with the thumb or finger, before increasing in width at the distal end 95 of the second support member 70 in order to provide sufficient support to the palm region of the wearer's hand.

The distal end or terminal 95 of the second support member 70 is formed into a domed portion 100, which has a spooned, bowled or hemispherical shape. The distal end or terminal end 95 of the second support member 70 is left free, i.e. it is not joined or connected to the first support member 10, other than via the part of the second support member 70 that curves from the first support member 10 between the thumb and forefinger, in use.

The domed portion 100 curves upwardly, e.g. towards the palmer arch 85 of the wearer's hand in use and/or toward the first support member 10. In this way, the domed portion 100 matches the contours of the palm of the wearer's hand in the palmer arch region 85, thereby providing greater support for the palm whilst minimising interference during use of the hand. In embodiments, the domed portion 100 is hollowed or partially hollowed. Optionally, the domed portion 100 can be covered by at least part of a removable cover 120 (see FIG. 8) and/or at least part or all of the domed portion 100, e.g. at least a side of the domed portion that is away from or opposite to the first support member and/or the hand, in use, can be coated or overmoulded with a conformable or pliant material, such as a polymeric material. This allows optimal contact with a gripped object to be made.

The second support member 70 is a rigid member and in this embodiment is integral with and/or formed from the same material as the first support member 10. However, it will be appreciated that the second support member 70 can instead be attached or fixed to the first support member 10 and/or formed from different material or using a different layup, e.g. to control the rigidity, flexion and/or other properties of the second support member 70.

Two pairs of fixing parts 40a', 40a", 40b', 40b" extend from opposite edges 45a, 45b of opposing curved parts 25a, 25b of the first support member 10, at longitudinally spaced apart locations along the first support member 10, such that the respective fixing parts 40a', 40a", 40b', 40b" of each pair oppose or face each other. In this way, in use, each of the fixing parts 40a', 40a", 40b', 40b" of each of the pairs extend part of the way around opposite sides of the forearm. The pairs of fixing parts 40a', 40a", 40b', 40b" are located such that, in use, one of the pairs of fixing parts 40a', 40a" is located behind the thumb, e.g. on an opposite side of the thumb to the second support member 70, and the other of the pairs fixing parts 40b', 40b" is located rearwardly of the other pair of fixing parts 40a', 40a", i.e. further up the forearm towards the elbow.

Each fixing part 40a', 40a", 40b', 40b" comprises a flange portion 50 that is integral with the first support member 10. Each flange portion 50 defines a slot 55 for receiving a detachable strap 60 therethrough. The strap 60 is formed from a suitable webbing and comprises an attachment mechanism 65, such as Velcro, preferably low-tack Velcro, for fixing the strap 60 to itself or to another strap 60 so that one or more straps 60 join opposing flange portions 50. In this way, in use, the strap 60 can extend from one fixing part 40a', 40a", 40b', 40b" of a pair of fixing parts around the lower surface of the forearm, though the corresponding slot 55 on the other fixing part 40a', 40a", 40b', 40b" of the pair. Thereafter, the strap 60 is fixable to itself along the bottom surface of the forearm using the attachment mechanism 65 in order to secure the strap 60 between the opposing pair of flanges 40a' and 40a", 40b' and 40b" and provide the closed configuration in which the support device 5 is secured to the forearm.

Beneficially, it will be appreciated that the rigid, composite or polymeric parts of the support device 5, i.e. the first support member 10, second support member 70 and the flanges 50 of the fixing parts 40a', 40a", 4-b', 40b" do not encircle or enclose the arm, hand or wrist of the wearer. In this way, it may be possible to get a good fit of the support device 5 to the arm, hand and wrist of the wearer but still securely attach the support device 5 and support the wrist at the required angle.

Figure 9:
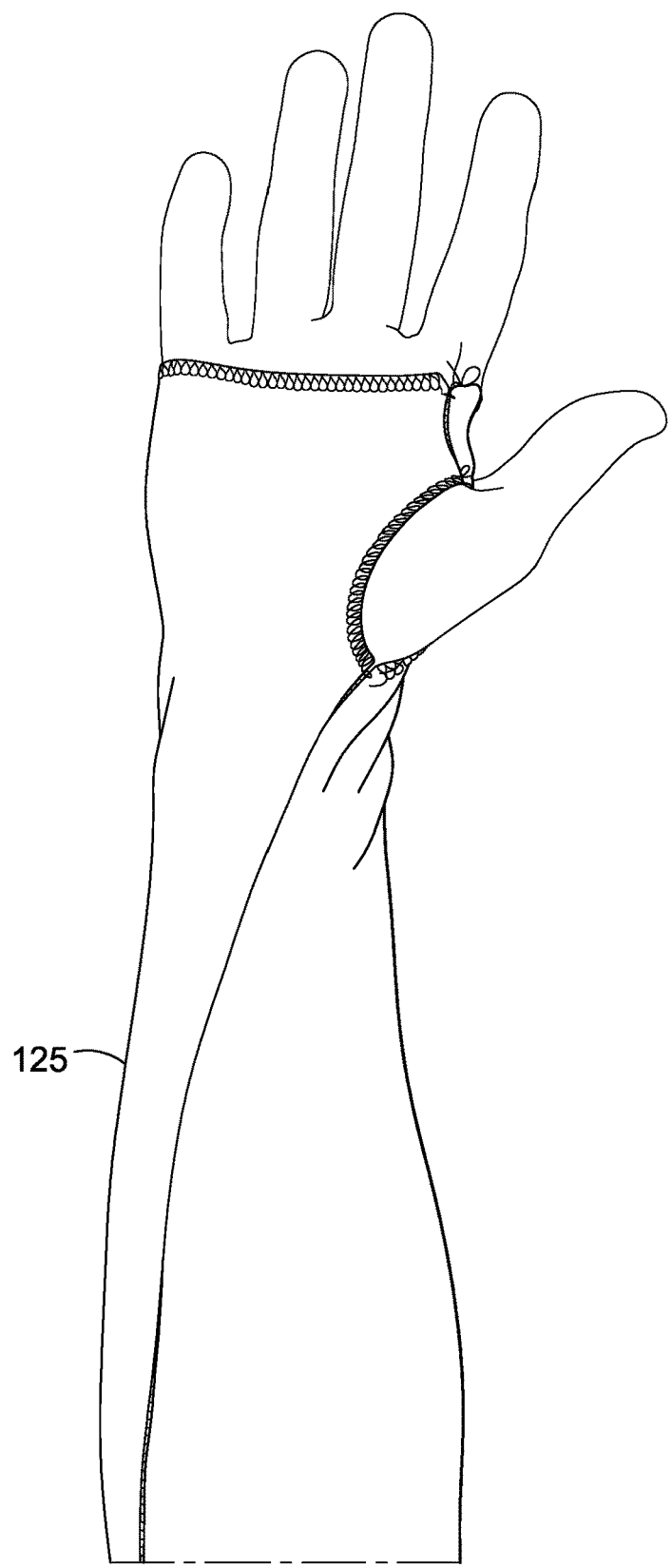
FIG. 9 is a bottom view of a sleeve for use with the wrist support of FIG. 1, in use.
Figure 10:
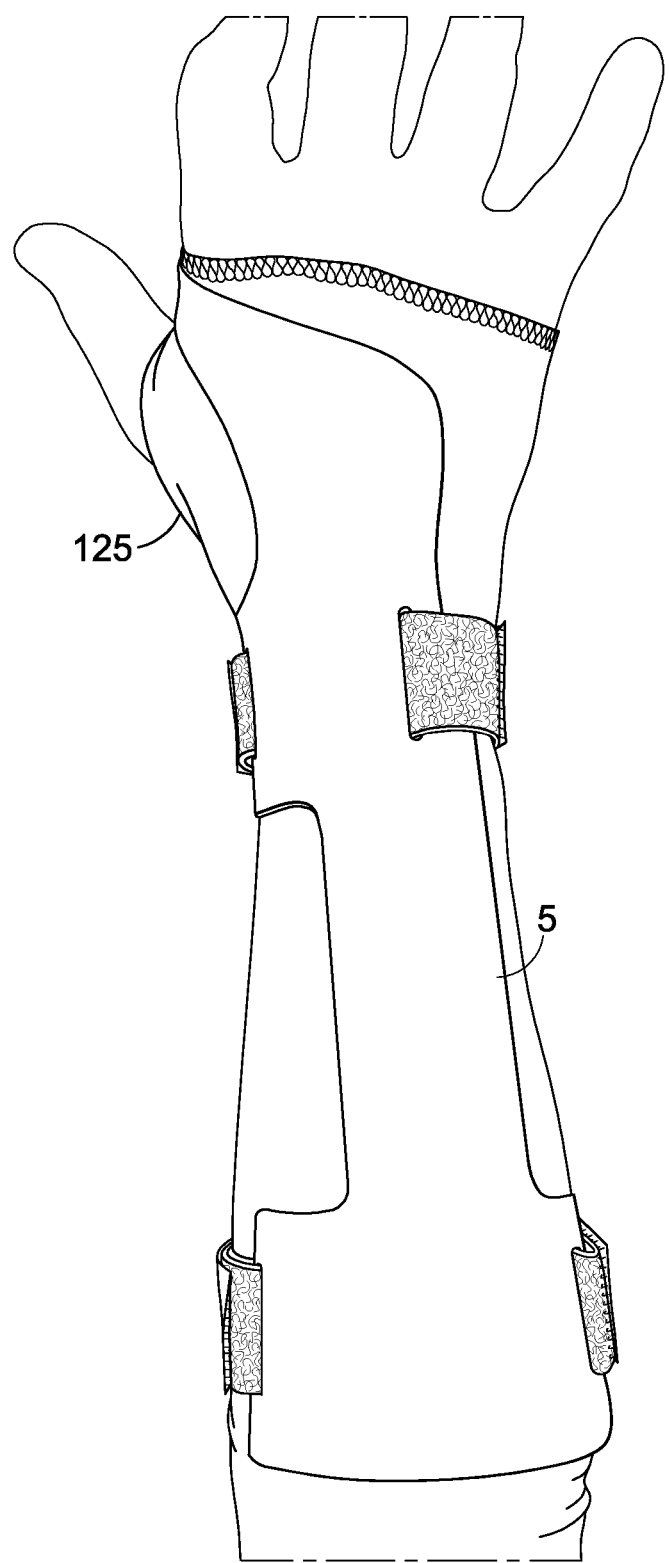
FIG. 10 is a top view of the wrist support of FIG. 1 in use with the sleeve of FIG. 9.

Optionally, the support device 5 is used with a sleeve 125 or cover 120 (see FIGS. 8 to 10) between at least part or all of the support device 5 and the wearer. The sleeve 125 or cover 120 could be fixed to the support device 5 and cover at least part of the support device 5, such as the second support member 70 (see FIG. 8) or could be worn on the hand, wrist and/or forearm of the wearer so as to sit between at least part of the support device 5 and the wearer (see FIGS. 9 and 10). The sleeve 125 or cover 120 can comprise, for example, one or more layers of fabric, padding such as gel, fibre or fabric padding or wadding, and/or the like.

The sleeve 125 is optionally removable from the support device 5. In this way, the fabric based sleeve (and also the removable straps 60) can be easily laundered or washed. The support device 5 is formed from materials that can be wiped clean, such as polymeric and/or composite materials. In this way, both the sleeve and the support device 5 can be easily cleaned.

In embodiments the sleeve covers at least some of an outer surface of the support device 5. The sleeve can be coloured, dyed, printed on and the like. In this way, an appropriate sleeve can be selected to match a skin colour or the colour of garments being worn by the wearer in order to lessen the visual impact and/or partially hide or camouflage the support device 5.

Beneficially, one or both of the support device 5 and/or sleeve 125 can be provided with one or more pockets, chambers and/or the like. The pockets or chambers can be used to retain heat or cool pads for example, in order to provide heating and/or cooling of selected areas. This may have therapeutic or pain relief effects, for example.

It should be understood that the embodiments described herein are merely exemplary and that various modifications may be made thereto without departing from the scope of the invention.

Figure 11:
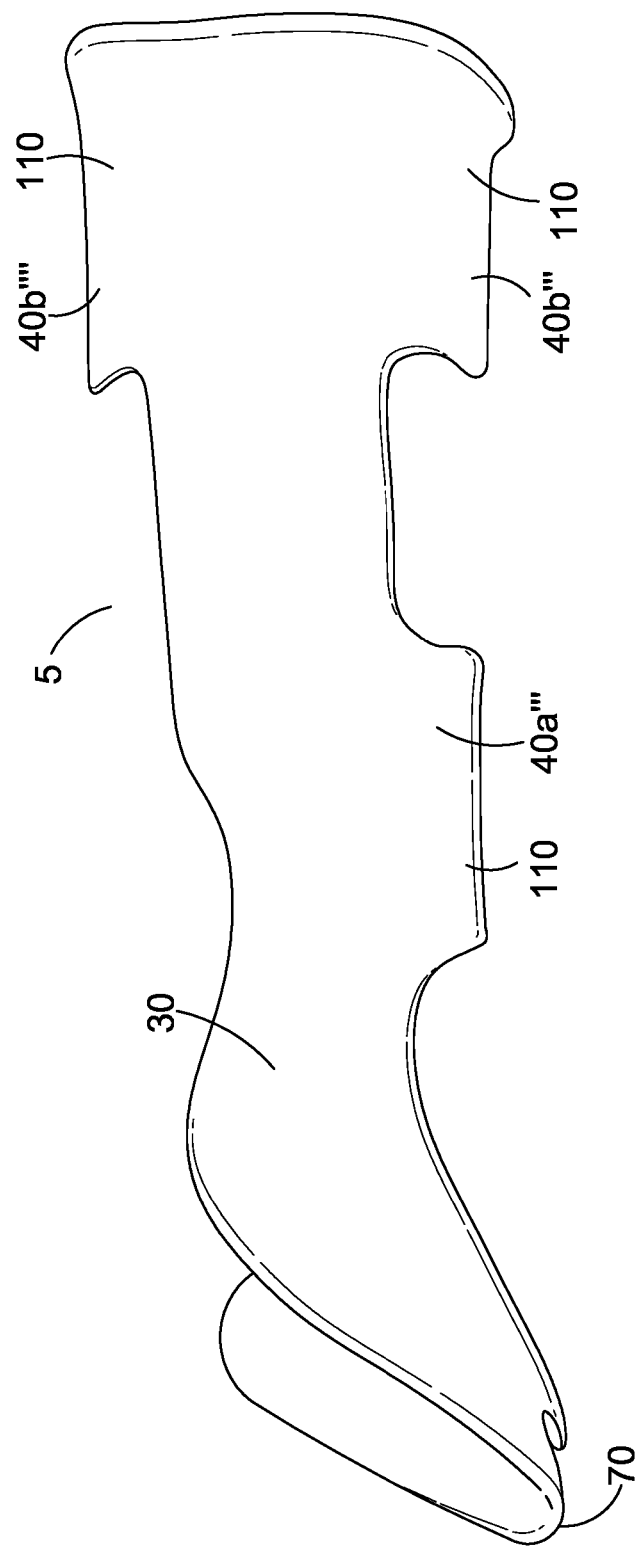
FIG. 11 is a top view of a wrist support.
Figure 12:
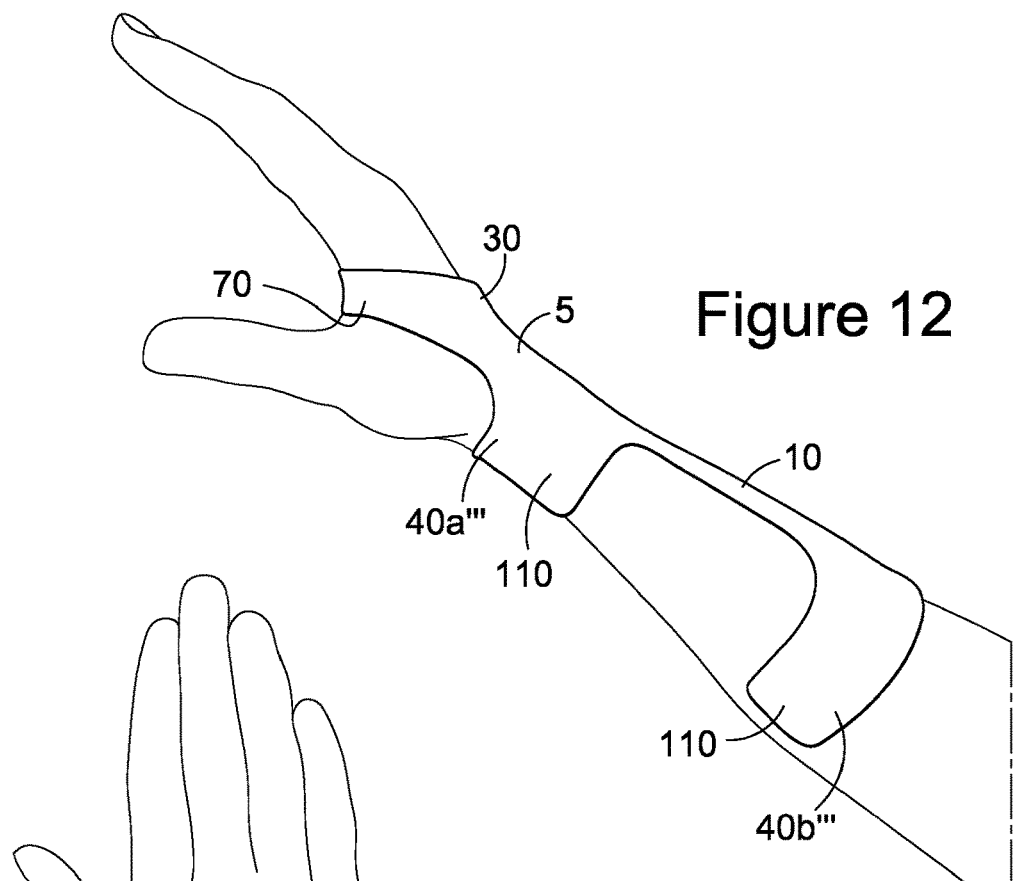
FIG. 12 is an elevation or side view of the wrist support of FIG. 11, in use.
Figure 13:
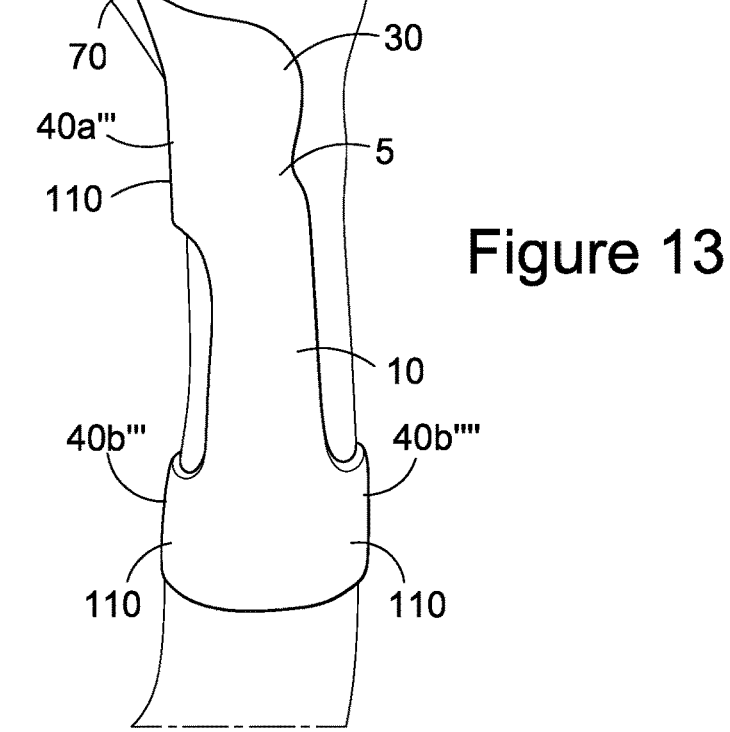
FIG. 13 is a top or plan view of the wrist support of FIG. 11.

For example, although embodiments described above comprise two pairs of fixing parts 40a', 40a", 40b', 40b" that use a strap 60 to attach support device 5 to the forearm of the wearer, it will be appreciated that one or more of the fixing parts 40a''' need not be provided in a pair, other numbers of fixing parts may be used and/or fixing arrangements other than straps 60 may be used. One example of such as device is shown in FIGS. 11 to 13. This device is similar to that shown in FIGS. 1 to 8 and 10 but differs in that only one fixing part 40a''' is provided towards the forward end 35 of the first support member 10, e.g. the end having the ramped or sloping portion 30. Advantageously, no fixing part or other rigid structure of the support device that extends to the ulnar side, e.g. an opposite side of the first support member 10 to the side to which the second support member 70 extends from the first support member 10, is provided on a forward or forwardmost part, end or half of the device. In other words, in use, the ulnar side of the front part of the forearm, wrist and hand is not covered, left open. Furthermore, fixing parts 40a''', 40b''', 40b'''' optionally comprise flexible flanges 110 that, in use, extend around the side of the forearm of the wearer to a location on a lower or under side of the forearm. The rearward fixing parts 40b''', 40b'''', i.e. those that are furthest from the ramped or sloping member 30 comprise a pair of opposing flexible flanges 110 that, in use, each extend around respective sides of the forearm to locations below the forearm but leave a gap between the underarm ends of the opposing flexible flanges 110 to allow the forearm to be inserted therethrough.

It will also be appreciated that other variations may be made to the support device 5. For example, the support device 5 described above is advantageously formed from a composite polymer material, such as a glass fibre/Nylon matrix composite material. However, it will be appreciated that other materials may be used such as carbon, aramid or glass fibre in a resin, polymer or epoxy matrix, polymeric materials such as PEEK, Polyethylene, acrylics, Polypropylene, PTFE, PET, and/or the like. In embodiments, at least the first and/or second support members 10, 70 may comprise a metallic core, such as a metallic bar or strip, coated with a polymeric, silicone or fabric material.

The shapes of the first and second support members 10, 70 are arranged to securely fit to the forearm, wrist and palm of the hand of the wearer and to securely and comfortably hold the wrist in a required position. However, it will be appreciated that the shape, structure and arrangement of the first and second support members 10, 70 and the fixing parts 40a', 40a", 40a'", 40b', 40b", 40b'", 40b"" can be varied or selected, e.g. in order to fit or match natural differences and variations in body shape and size between different wearers.

By providing rigid first and second support members 10, 70, wherein the first support member 10 is locatable on an upper surface of the forearm and wrist in use and the second support member 70 extends from the first support member round to terminate at a palm side of the hand, preferably extending between the thumb and index finger, the support device 5 can be made with minimal rigid structure. This minimises interference between the support device 5 and the hand and/or a held or grasped object and lessens the impact of the support device 5 on the usability of the hand whilst at the same time securely holds the wrist in the required position.

The rigid structure of the support device 5 (e.g. the first and second support members 10, 70 and the flanges of the fixing parts) does not encircle or enclose the arm, wrist or hand. For example, the first and second support members 10, 70 define an open structure. In the example above, the open structure is achieved by the second support member 70 being left free at its distal or terminal end 95 and the first support member 10 being left open, i.e. being arranged to only cover part, e.g. an upper part and/or a top surface, of the forearm in the circumferential direction, in use. As such, the support device 5 may be made to better fit a wide range of arm/hand sizes.

Since the second support member 70 is left free at its distal or terminal end 95, and the forearm and thumb of the wearer is not encircled by rigid structure in use, with the first support member 10 only being provided on an upper part or topmost surface of the forearm and wrist, the user is more able to perform action and is more dexterous than with traditional supports, whilst still being provided with the necessary support of the wrist.

Since the second support member 70 is arranged to extend between the thumb and index finger, the support device 5 may be made to "self-locate" in the correct position, simply by inserting the user's hand into the support device 5. This arrangement also limits the motion of the wrist joint in a lateral, transverse or radial direction.

By providing at least one flange 50, 110 of a fixing part 40a', 40a", 40a'" such that it locates behind the thumb or wrist in use (i.e. on an opposite side of the thumb to the second support member 70), for example such that the thumb is located or locatable between the second support member 70 and a flange or fixing part 40a', 40a", 40a'", the support device 5 may more securely self-locate in the correct position simply by inserting the user's hand into the support device 5.

The second support member 70 reduces in width in an intermediate portion 90 yet comprises a wider domed portion 100 at its distal or terminal end 95 that domes or curves up toward the palm of the hand/first support member 10 in use, so as to conform to and support the palmer arch 85 of the wearer. In this way, the wrist of the wearer may be more securely and comfortably supported in the required position whilst minimising the bulk of the support device 5 in the region of the wearer's palm in order to minimise interference when the wearer uses the hand.

The above examples relate to a wrist-hand splint. However, it will be appreciated that similar concepts may be applied to other joint supports or splints, such as knee or ankle splints. In these cases, the fixing parts can mount the splint on the upper or lower leg and the first support member can extend over the knee and/or ankle. An appropriately angled ramped or sloping part can be provided at the knee/ankle to control the required angle of the joint. The second support member can be configured to extend around to an opposite side of the lower or upper leg or foot (as appropriate) to the first support member such that the first support member controls motion of the joint in a first direction and the second support member controls motion of the joint in a second direction. The same concept could be applied to other joints/body parts.

In the above description, terms such as forward, backward, above and below are used. It will be appreciated that these relate to directions of the support device 5 when in use on the forearm of the wearer.

In relation to the support itself, forwardly and backwardly are equivalent to directions in the longitudinal direction 115 of the support device 5/first support member 10, with the ramped or sloping end 30, 35 of the support device 5/first support member 10 being the forward end and the downward direction being a direction perpendicular to both the longitudinal 115 and lateral/transverse 15 directions of the support device 5, with downward being the direction in which the sides of the first support member curve and in which the second support member and/or fixing parts are located or extend relative to the first support member.

In relation to the wearer, forwardly is used to indicate towards the hand or fingers of the wearer, rearwardly is used to indicate towards the elbow of the wearer, below or under is used to indicate towards or at an underside of the forearm or palm of the wearer and above or upwardly is used to indicate towards or at an upper surface of the forearm and/or the back of the hand of the wearer.

It will be appreciated that, in use, the longitudinal direction 115 of the support and/or first support member runs lengthwise along the forearm of the wearer, i.e. in a direction between the elbow and hand. In other words, the longitudinal direction 115 of the support device will generally be parallel to or coincident with the longitudinal direction of the forearm, in use. It will be appreciated that, in use, the lateral/transverse direction 15 of the support and/or first support member runs across the forearm or wrist, i.e. in a direction between from one side of the fore arm or wrist to the other side. Given that the support device is arranged to be mounted in a very specific arrangement on the forearm and wrist/hand of the wearer, it would be straightforwardly apparent to a person skilled in the art which directions are in a forward or hand side direction, rearward or elbow side direction, above or top direction or below or bottom direction.

For example, forward or forwardly as used herein relates to a direction generally extending in a longitudinal direction 115 of the first support member/forearm and toward the end of the first member 10 having the ramped or the sloping portion from the opposite end of the support device 5, e.g. running toward a hand/knuckles of the wearer and away from an elbow of the wearer, in use. Below or beneath is used to describe a direction perpendicular to both the longitudinal 115 and transverse 15 directions of the first support member in a direction generally from the top of the forearm to the bottom of the forearm or in a direction from the back of the hand towards the palm of the hand, in use. Above or upwardly is used to describe a direction perpendicular to both the longitudinal 115 and transverse 15 directions of the first support member in a direction generally from the bottom of the forearm to the top of the forearm or in a direction from the palm of the hand towards the back of the hand towards, in use.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of any claims. The applicant indicates that aspects of the invention may consist of any such individual feature or combination of features. In view of the foregoing description it will be evident to a person skilled in the art that various modifications may be made within the scope of the invention, and that the description provides only one example embodiment of how the invention may be implemented.

The invention claimed is:

1. A support for supporting a wrist of a wearer, the support comprising: at least one rigid first support member for locating on an upper side of a forearm and wrist in use,
   at least one fixing device for attaching the support to the wearer, and at least one rigid second support member extending at an angle from the at least one rigid first support member, wherein:
   the at least one rigid first support member comprises:
      a longitudinally extending rigid center part that is configured to extend rigidly along, and sit on top of, at least part of the forearm and part of the wrist of the wearer; and
      a rigid sloping section forming an end of the at least one rigid first support member, the rigid sloping section being configured to cover an upper side of part of the wrist and at least a portion of an upper hand, the rigid sloping section sloping in a longitudinal direction of the at least one rigid first support member, the longitudinally extending rigid center part transitioning into the rigid sloping section such that the rigid sloping section is adjacent and angled to the longitudinally extending rigid center part and the at least one rigid first support member as a whole is non-elastic;
   the at least one rigid second support member comprises at least a first part and a second part;
   the first part of the at least one rigid second support member is integral with or fixed to the rigid sloping section of the at least one rigid first support member and extends obliquely away from the rigid sloping section of the at least one rigid first support member that the at least one rigid second support member is integral with or fixed to, at least partly in a direction that is perpendicular to both the longitudinal direction and a lateral direction of the at least one rigid first support member, to the second part of the at least one rigid second support member, which extends generally laterally from the first part;
   the at least one rigid second support member has a terminal or distal end that is configured to support a palm of a hand of the wearer such that at least part of the hand lies between the terminal or distal end of the at least one rigid second support member and the rigid sloping section of the at least one rigid first support member in use;
   the at least one rigid second support member arranged to extend along the palm of the wearer in use and is free at said terminal or distal end thereof; and
   the support is configured such that, in use, an ulnar side of the wrist and hand of the wearer are not covered by the support and are left open;
   wherein the rigid sloping section is angled between 10 and 20 degrees from an adjacent part of the at least one rigid first support member.

2. The support according to claim 1, wherein a portion of the at least one rigid second support member that is located towards, adjacent or is connected to the at least one rigid first support member reduces in width towards an intermediate or middle portion of the at least one rigid second support member.

3. The support according to claim 2, wherein the intermediate or middle portion of the at least one rigid second support member is located proximate or adjacent a thumb or between the thumb and index finger in use.

4. The support according to claim 2, wherein a width of the at least one rigid second support member increases from the intermediate or middle portion towards or at a distal end of the at least one rigid second support member.

5. The support according to claim 1, wherein the second part of the at least one rigid second support member extends generally parallel to at least part of the at least one rigid first support member.

6. The support according to claim 5, wherein the second part of the at least one rigid second support member is spaced apart from the at least one rigid first support member forwardly and in a direction that is perpendicular to both the longitudinal direction and a lateral direction of the at least one rigid first support member.

7. The support according to claim 1, wherein at least part or all of at least one of the at least one rigid first or the at least one rigid second support member comprises one or more portions or layers formed from a different material than one or more other portions or layers of the at least one of the at least one rigid first or the at least one rigid second support member.

8. The support according to claim 7, wherein at least part of at least one of the at least one rigid first or the at least one rigid second support member comprises at least one of a softer or a more pliable or a deformable material and at least part of at least one of the at least one rigid first or the at least one rigid second support member comprises at least one of a rigid or a less pliable or deformable material, wherein the rigid, less pliable or deformable material is comprised in an inner material, portion or layer and the softer, more pliable or deformable material is comprised in an outer material, portion, coating or layer.

9. The support according to claim 1, wherein at least part of the support is provided with or covered by at least one sleeve, wherein the at least one sleeve is at least one of removable or detachable from the support.

10. The support according to claim 9, wherein the at least one sleeve comprises at least one of an under sleeve, located or locatable between at least part of at least one of the at least one rigid first or the at least one rigid second support members and the wearer or an over-sleeve configured to cover at least part or all of an outer surface of the support.

11. The support according to claim 1, wherein the support is configured to limit at least one of flexion, extension, or radial deviation of the wrist.

12. The support according to claim 1, wherein, in use, the at least one rigid second support member is arranged to extend between a thumb and index finger of the wearer, along at least part of the palm to a central portion of the palm or palmer arch of the wearer.

13. The support according to claim 1, wherein the support is configured such that, in use, the rigid sloping section is provided at, over or covering at least one of (a) at least a part of at least one side of the wrist or (b) a part of at least one side of the palm of the hand.

14. The support according to claim 1, wherein the at least one rigid second support member is provided at an end of the at least one rigid first support member.

15. The support according to claim 1, wherein the at least one rigid second support member extends from the rigid sloping section of the at least one rigid first support member.

16. The support according to claim 1, wherein a distal end of the at least one rigid second support member comprises at least one of a rounded, domed, or hemispherical portion.

17. The support according to claim 1, wherein the support comprises one, two or more pairs of fixing devices, wherein one or more or each pair of fixing devices comprises opposing fixing devices extending from opposing sides of the at least one rigid first support member.

18. The support according to claim 1, wherein the at least one fixing device comprises at least one of (a) at least one flange, (b) at least one slot, or (c) at least one other attachment for mounting a strap or other fixing, and the strap or other fixing comprises at least one fixing mechanism for releasably fixing the strap to itself, another strap and/or flanges of one, two or more fixing devices.

19. The support according to claim 1, wherein the support is configured such that a thumb of the wearer is located or locatable, in use, between one of the at least one fixing device and the at least one rigid second support member.

20. The support according to claim 1, wherein at least one of the at least one rigid first or the at least one rigid second support members comprises at least one of a metallic member, a polymeric or silicone member, coating or portion, or a composite member or portion.

21. The support according to claim 1, wherein the support is configured such that at least a forward side part and/or a part of the support that is toward or comprises the at least one rigid second support member comprises no fixing devices or other rigid structure extending from a lateral side of the at least one rigid first support member opposite to that from which the at least one rigid second support member extends and/or to an ulnar side of the hand, wrist and/or forearm, in use.

22. A sleeve or cover configured to be mounted to or used with the support according to claim 1.

23. The sleeve or cover of claim 22, wherein the sleeve or cover is releasably attachable to the support.

24. The sleeve or cover according to claim 22, wherein the sleeve or cover comprises an under sleeve or cover located or locatable between at least part of the at least one rigid first and/or the at least one rigid second support members and the wearer, in use, and/or an over-sleeve or cover configured to cover at least part or all of an outer surface of the support.

25. A method of use of the support of claim 1 for holding at least one of a wrist or a hand in a given position, the method comprising fitting at least part of the support to at least one of a forearm or a wrist such that the at least one rigid first support member is provided on an upper surface of the forearm and/or the wrist and locating the at least one rigid second support member such that it extends between a thumb and an index finger to a location against, proximate or below the palm of the hand.

26. A method of manufacturing a support according to claim 1, the method comprising moulding, laying material up on a former or template, 3D printing, injecting, bending, bonding, at least one of fixing or cutting material so as to form the at least one rigid first support member and the at least one second support member extending at an angle from the at least one rigid first support member such that the at least one rigid second support member extends and/or curves forwardly and downwardly from the at least one rigid first support member and then laterally relative to the at least one rigid first support member.

* * * * *